(12) United States Patent
Wolff et al.

(10) Patent No.: US 7,713,489 B2
(45) Date of Patent: May 11, 2010

(54) EXPERIMENTAL DEVICE FOR THE STUDY AND THE EXTRAPOLATION OF PROCESSES IN A REACTIVE SIMULATED MOVING BED

(75) Inventors: Luc Wolff, Chaponnay (FR); Damien Leinekugel Le Cocq, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 440 days.

(21) Appl. No.: 11/785,912

(22) Filed: Apr. 20, 2007

(65) Prior Publication Data

US 2008/0038157 A1      Feb. 14, 2008

(30) Foreign Application Priority Data

Apr. 21, 2006    (FR) .................................. 06 03690

(51) Int. Cl.
*B01J 19/00*        (2006.01)
*B01J 10/00*        (2006.01)
(52) U.S. Cl. ...................... 422/130; 422/189; 422/190; 422/191; 422/193; 585/820; 585/826; 585/834
(58) Field of Classification Search ................. 422/189, 422/190, 191, 193, 130; 585/820, 826, 834
See application file for complete search history.

(56) References Cited

U.S. PATENT DOCUMENTS

| 5,744,683 | A | 4/1998 | Dandekar et al. |
| 5,877,373 | A | 3/1999 | Zinnen et al. |
| 6,265,626 | B1 * | 7/2001 | Carr et al. ................... 568/915 |

OTHER PUBLICATIONS

Abunasser N., Wankat P.C.: "One-Column Chromatograph with Recycle Analoguous to a Four-Zone Simulated Moving Bed"; Industrial & Engineering Chemistry Research; vol. 42, No. 21; Oct. 15, 2003; pp. 5268-5279; XP002413051.

* cited by examiner

*Primary Examiner*—Walter D Griffin
*Assistant Examiner*—Lessanework Seifu
(74) *Attorney, Agent, or Firm*—Millen, White, Zelano & Branigan, P.C.

(57) ABSTRACT

The invention relates to an original experimental device for the study and the validation of processes in a reactive simulated moving bed, as well as the method that makes possible the exploitation of the results obtained from said device.

This device consists of one or two columns and a number of storage tanks.

9 Claims, 6 Drawing Sheets

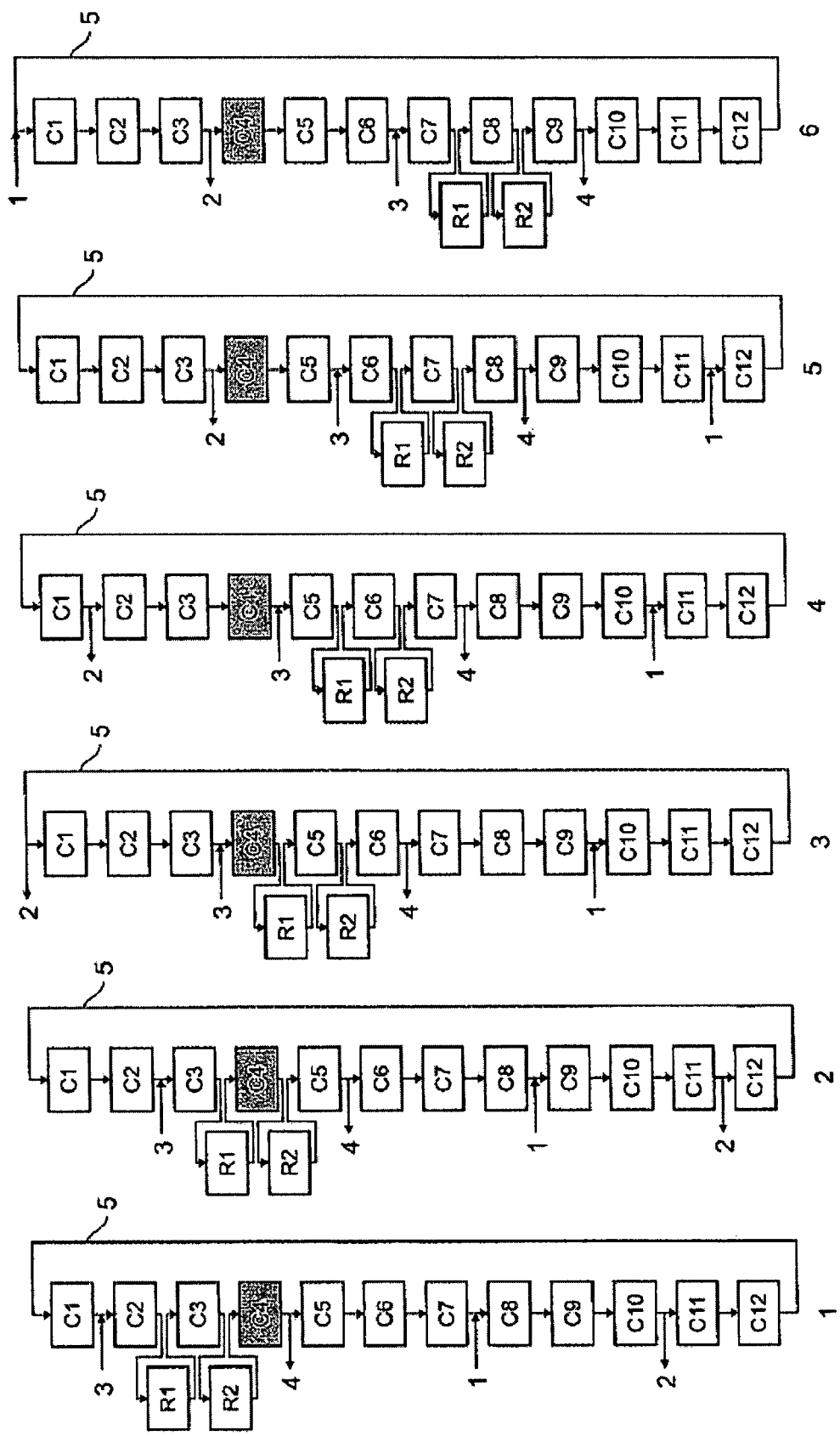
Figure 3.1

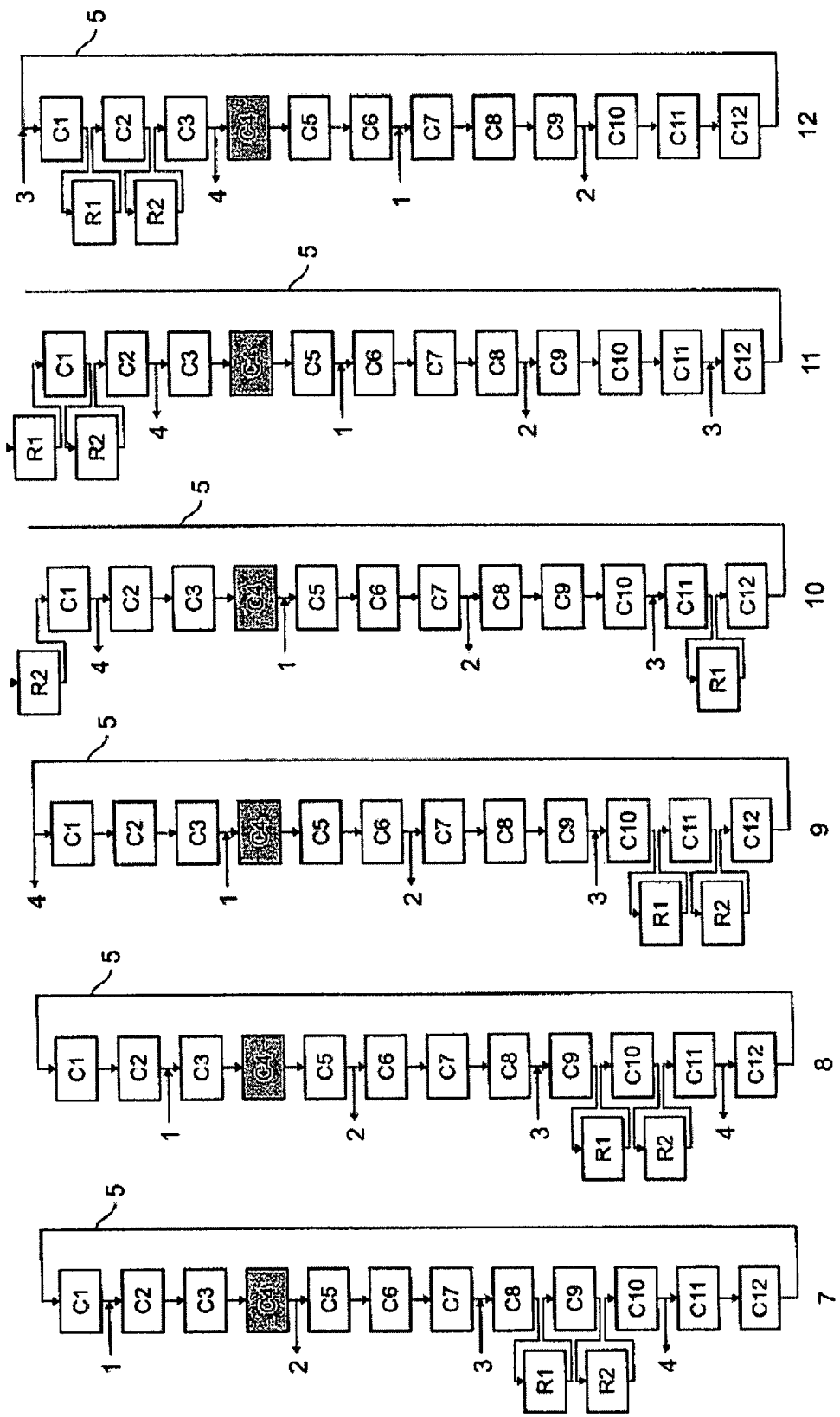
Figure 3.2

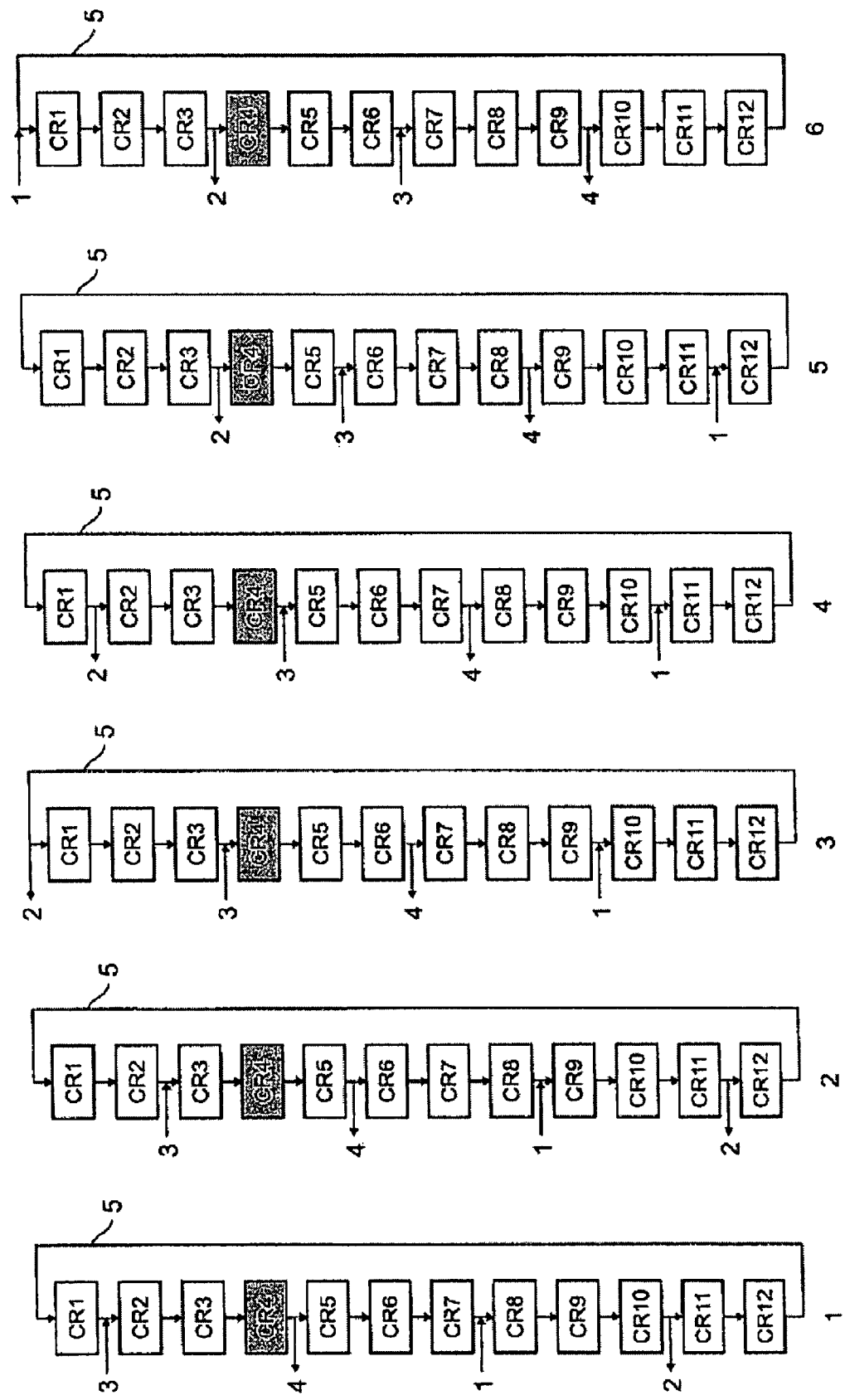
Figure 4.1

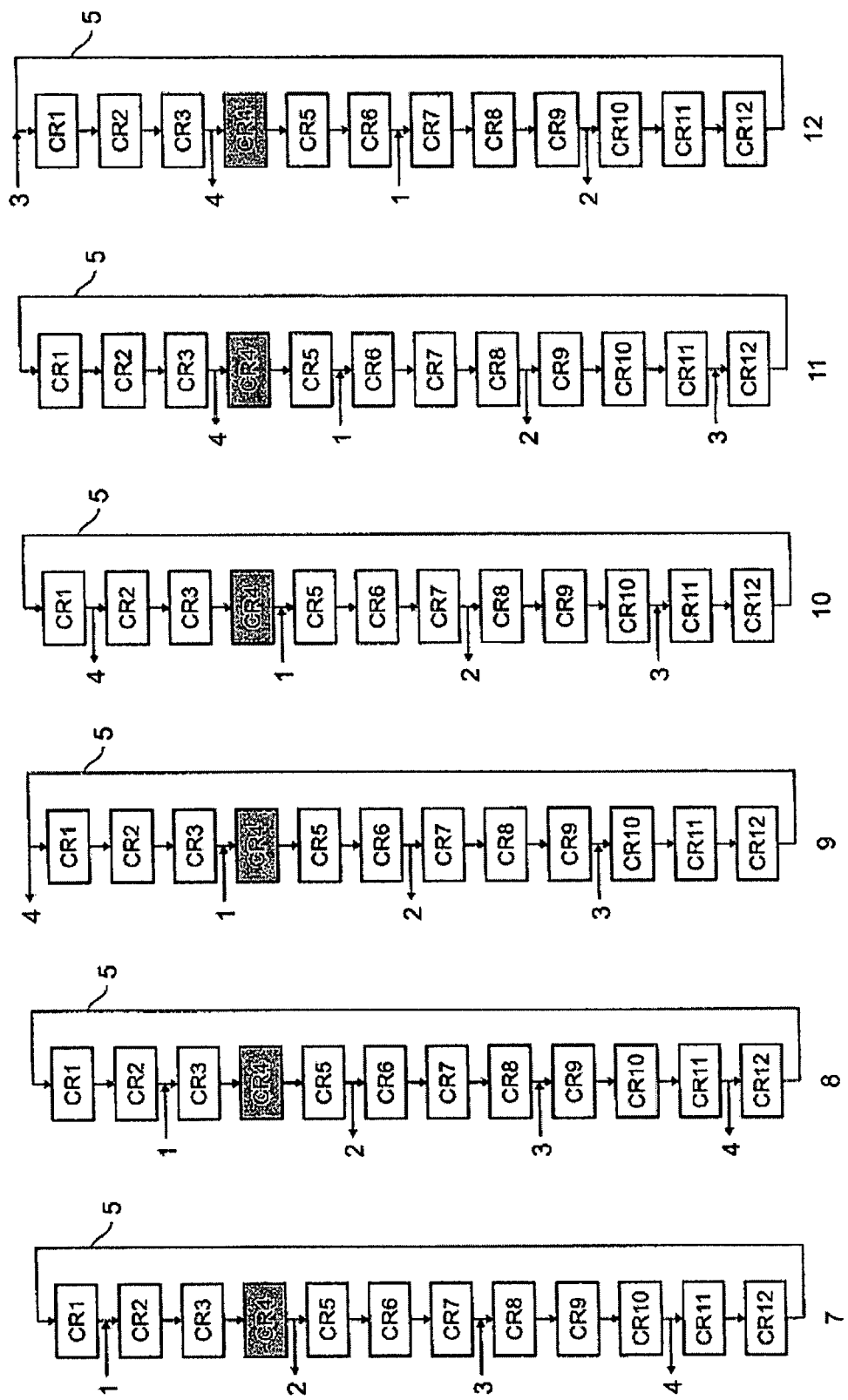
Figure 4.2

EXPERIMENTAL DEVICE FOR THE STUDY AND THE EXTRAPOLATION OF PROCESSES IN A REACTIVE SIMULATED MOVING BED

FIELD OF THE INVENTION

The invention is part of the field of experimental tools allowing the study of separation processes, optionally with chemical reaction, implemented in a reactive simulated moving bed.

Let us recall that the simulated moving bed is a fixed-bed reactor comprising a number of inputs (for the feedstock and the eluant) and outputs (for the extract and the raffinate) that are distributed over its entire length, which are regularly offset over time by adhering to their relative positions so as to sweep all possible positions and in this way to create an imaginary movement of the bed, hence the name simulated moving bed. There will be found, for example, a detailed description of the simulated moving bed concept in the patent FR 2 721 528. The simulated moving bed is employed in particular in the petrochemical industry for the separation of, for example, xylenes, n-paraffins mixed with branched and aromatic hydrocarbons, and olefins mixed with paraffins. The simulated moving bed is also employed in other industries, such as, for example, that of sugar, and for several years in the pharmaceutical industry. All of the simulated moving bed processes are covered by this invention.

EXAMINATION OF THE PRIOR ART

The integration of a balanced reaction leading to one or more products (for example, A ↔ B or A(+B) ↔ C+D), catalyzed by a heterogeneous catalyst, within a separation unit by adsorption in a simulated moving bed, is well known from the prior art.

In the case of a reaction of type A(+B) ↔ C+D providing two products separated by adsorption, it is possible to mention the article that is published by Lode et al. (2001, Chem. Eng. Sci., Vol. 56, pages 269-291), which stipulates the implementation of a simulated moving bed on the laboratory scale, applied to the esterification of acetic acid by methanol for producing methyl acetate. In this case, catalyst and adsorbent are mixed in the beds of the unit.

In the case of a reaction of type A ↔ B, it is possible to cite, for example, the article that was published by Hashimoto et al. in 1983 in the journal of Biotechnology and Bioengineering (Volume 25, pages 2371-2393), in which the implementation of the reactive simulated moving bed applied to the isomerization of glucose into fructose and to the isomerization of xylenes into paraxylene is stipulated.

Several documents of the prior art describe the implementation of the reactive simulated moving bed processes for a particular application.

For example, the patent U.S. Pat. No. 5,449,696 describes a reactive simulated moving bed process in which adsorbent and catalyst are mixed, whereby the process is applied to the production of methanol from carbon monoxide and hydrogen.

The patent U.S. Pat. No. 6,005,153 describes a process for transalkylation of an alkylaromatic compound with 9 or 10 carbon atoms to produce at least one alkylaromatic compound with 8 carbon atoms in a reactive simulated moving bed in which adsorbent and catalyst are mixed.

None of the cited documents provide information relating to an experimental device that makes it possible to study the claimed process on a pilot scale.

In a general manner, the documents that describe an experimental assembly for the study of a reactive simulated moving bed process, both for reactions leading to a single product (for example A ↔ B) and for reactions that lead to several products (for example A(+B) ↔ C+D), will produce a great complexity of the experimental tool that is used, in particular in terms of the number of columns, and a limitation of the experimental tool to a quite particular application or to a particular type of reaction (A ↔ B or A (+B) ↔ C+D).

Several documents of the prior art describe units that are composed of a single column, whose behavior is comparable to that of a simulated moving bed.

The articles published by Abunasser et al. (2003, Ind. Eng. Chem. Research., Vol. 42, pages 5268-5279) and by Abunasser and Wankat (2004, Ind. Eng. Chem. Research., Vol. 43, pages 5291-5299) describe a so-called "One-Column" system, i.e., a single-column system in which the column follows the conventional cycle of the simulated moving bed, except that the fluid that is obtained at the outlet of the column is stored in a tank before being reinjected into the inlet of the column.

In these documents, the behavior of the single-column system is compared to that of a simulated moving bed.

It is shown in particular there that the two systems have similar behaviors when a large number of fluid storage tanks are used.

The article that is published by Mota and Araújo (2005, AIChE Journal, Volume 51, pages 1641-1653) describes a variant of this system, using a storage tube in which the fluid flows according to a piston flow, making it possible to come close to the behavior of the simulated moving bed process.

These references therefore describe a device that comprises only one column and a number of intermediate storage tanks that make it possible to recycle, in a periodic and offset way over time, the effluent from the outlet of the column to the inlet of the latter so as to simulate a counter-current. In return, the authors do not suggest any implementation of this system for the study of the reactive simulated moving bed processes. The authors compare the performances of their single-column device with those of the simulated moving bed so as to optimize the operating parameters of their single-column device, the objective being that said device can achieve performance levels that are similar to those of the simulated moving bed.

This invention describes a new experimental device that makes it possible to study the reactive simulated moving bed processes by using at most two columns, regardless of the type of reaction used.

Thus, this device offers the advantage relative to the prior art of consisting of a small amount of equipment, while allowing the implementation of all types of reactions.

SUMMARY DESCRIPTION OF THE FIGURES

FIGS. 3.1 and 3.2 show the principle of operation of a reactive simulated moving bed unit on which it is desired to model the behavior by means of the device according to the invention in its first variant. This unit comprises 12 adsorbent beds (denoted as C1 to C12) and 2 catalyst beds (denoted as R1 and R2). This unit is specifically adapted to the case of a reaction that leads to a single product (for example, A ↔ B) that it is desired to recover in pure form in the extract (E).

The 12 stages of the cycle have been shown and numbered from 1 to 12 in each stage. The passage from one stage to the next consists in shifting by one bed the injection points of feedstock (C) and eluant (or desorbent) (S) and the draw-off points of the extract (E) and the raffinate (R).

FIGS. 4.1 and 4.2 show the principle of operation of a reactive simulated moving bed unit on which it is desired to model the behavior by means of the device according to the invention in its second variant. This unit comprises 12 beds that are filled with a mixture of adsorbent and catalyst (denoted as CR1 to CR12). This unit is specifically adapted to the case of a reaction that leads to two or more products in which it is desired to recover in the extract (E) as pure a retained product as possible.

SUMMARY DESCRIPTION OF THE INVENTION

This invention consists of an experimental device that makes possible the study of the processes that operate in a reactive simulated moving bed, whereby said device is associated with a model that makes possible the exploitation of the results for purposes of sizing an industrial or pilot unit that operates in a reactive simulated moving bed.

This invention breaks down into two variants.

Figure 1:
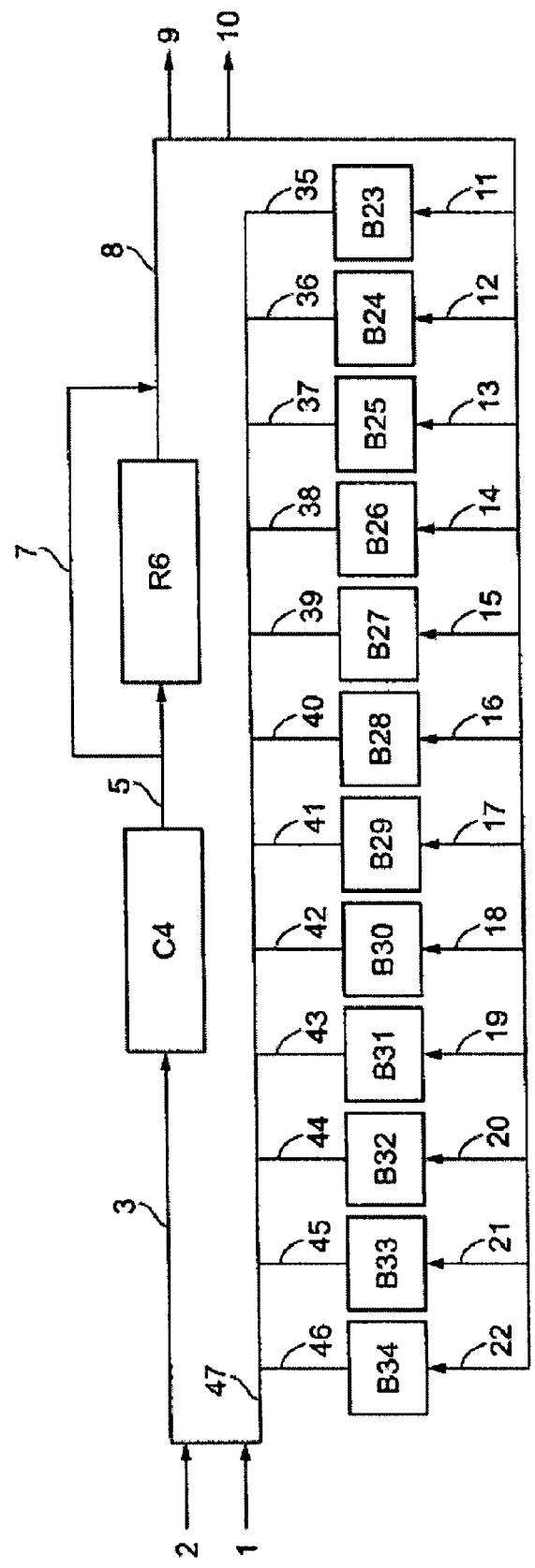
FIG. 1 shows a diagram of the device according to the first variant of the invention for balanced reactions leading to a single product or to several products.

In the first variant shown by FIG. 1, the system comprises a first column (C4) filled with adsorbent and a second column (R6) filled with catalyst, whereby the two columns can operate under different operating conditions. The first column is called an adsorption column, and the second column is called a reactive column.

This first variant corresponds to the case of a reaction that leads to a single effluent (for example, A ↔ B), or else to the case where the operating conditions of the reaction are very different from those of the separation.

In this first variant, the reactive zone is therefore separated from the adsorption zone.

In the case of a balanced reaction that leads to a single effluent, the reactive column can be short-circuited by means of the line (7) so as to avoid the reverse reaction phenomenon.

Figure 2:
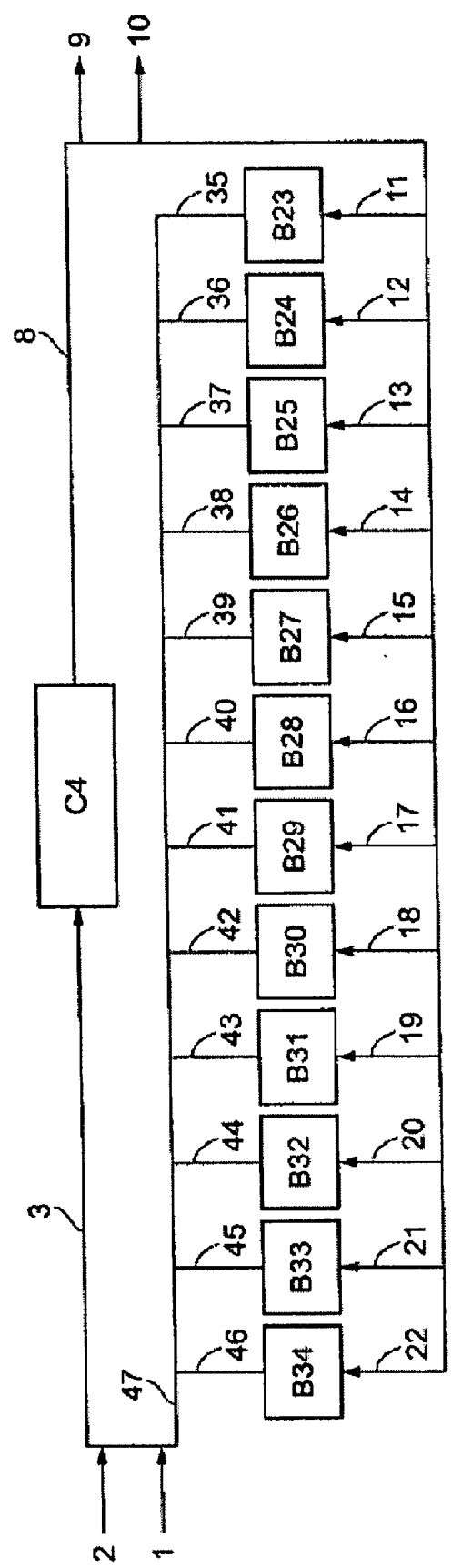
FIG. 2 shows a diagram of the device according to the second variant of the invention for any type of balanced reactions leading to several products. The numbers of flows and elements are the same in FIGS. 1 and 2 when they designate similar flows or elements in the sense where they occupy the same positions in the two figures.

In the second variant shown by FIG. 2, the system comprises a single column that is filled by an adsorbent-catalyst (CR4) mixture. This second variant corresponds to the set of cases that are not covered by the first variant, in particular the quite general case of a reaction that leads to two or more products, for example A (+B) ↔ C+D) that it is desired to separate by adsorption.

The two variants call upon a certain number of storage tanks (denoted as B23 to B34) whose minimum number is at least equal to a number of zones of the unit to be studied and preferably greater than the number of beds of the unit to be studied. The concepts of beds and zones will be clarified in the detailed description.

According to the first variant, the invention can be defined as an experimental device for the study and the extrapolation of an industrial or pilot unit that operates in a reactive simulated moving bed that comprises a first column (C4) that contains the adsorbent, a second column (R6) that contains the catalyst and a number of tanks (B23 to B34) that are used in the supply of the adsorption column (C4) and in the storage of the effluent that is obtained from the catalytic column (R6), except for certain stages of the cycle where said catalytic column is short-circuited by means of the line (7), whereby the device operates according to a cycle that is defined by the fact that with each stage n of said cycle, with the exception of the latter, the adsorbent column (C4) is supplied by the contents of the tank that has been filled by the flow of output from the column (R6) (or by the flow of output from the column (C4) when the column (R6) is short-circuited), corresponding to the stage (n+1) of the preceding cycle, and by the fact that in the last stage of the cycle, the adsorbent column (C4) is supplied by the contents of the tank that has been filled by the flow of output from the column (R6), (or by the flow of output from the column (C4) if the column (R6) is short-circuited), corresponding to the first stage of the preceding cycle.

According to the second variant, the invention can be defined as an experimental device for the study and the extrapolation of an industrial or pilot unit that operates in a reactive simulated moving bed in which the column that contains the adsorbent and the column that contains the catalyst are combined in a single column (CR4) that contains a mixture of adsorbent and catalyst, whereby said device contains a number of tanks (B23 to B34) used in the supply of the column (CR4) and in the storage of the effluent that is obtained from said column and whereby the cycle of the device is defined by the fact that in each stage n of said cycle, with the exception of the latter, the adsorbent column (CR4) is supplied by the contents of the tank that has been filled by the flow of output from the column (CR4) that corresponds to the stage (n+1) from the preceding cycle, and by the fact that in the last stage of the cycle, the adsorbent column (CR4) is supplied by the contents of the tank that has been filled by the flow of output from the column (CR4) that corresponds to the first stage of the preceding cycle.

DETAILED DESCRIPTION OF THE INVENTION

So as to properly understand the different stages of a cycle and the concept of zones, the nomenclature that is used is specified in a first step.

The abbreviation LMS means simulated moving bed. In a general manner, the adsorption column (also called adsorber) consists of several identical beds, each bed being delimited by an injection point and a draw-off point, knowing that these injection and draw-off points are used only at a certain moment of the cycle.

The feedstock and the eluant are injected at two separate points of the adsorber.

The raffinate and the extract are drawn off at two separate points of the adsorber, themselves separate from the two injection points. A set of consecutive beds delimited at one of its ends by an injection or draw-off point and at the other end by, respectively, a draw-off or injection point is called a zone.

At any time, at least four flows, two separate input flows, generally the feedstock (C) and the eluant (S), and two separate output flows, the extract (E) and the raffinate (R), therefore travel through the adsorber.

In some cases, there may exist several injections of eluant or feedstock and/or several draw-offs of extract or raffinate. In the description below, for reasons of clarity, only a unit comprising two injection points, one for the feedstock, the other for the eluant, and two draw-off points, one for the extract, the other for the raffinate, therefore comprising four zones, will be considered.

An LMS cycle is defined from an initial position of injection and draw-off points and corresponds to the coordinated movement of these points along the adsorber, from bed to bed until the initial position is found again.

A stage of the cycle is defined by an elementary movement from one bed of the injection and draw-off points along the adsorber.

A cycle will therefore comprise a finite number of stages, corresponding to the total number of beds of the adsorber.

The adsorber is generally subdivided into zones. These zones are defined in the following manner:

Zone 1: Zone of the adsorber located between the injection of the desorbent and the draw-off of the extract;

Zone 2: Zone of the adsorber located between the draw-off of the extract and the injection of the feedstock;

Zone 3: Zone of the adsorber located between the injection of the feedstock and the draw-off of the raffinate;

Zone 4: Zone of the adsorber located between the draw-off of the raffinate and the injection of the desorbent.

It involves the description of an adsorber that operates in 4 zones, but it is possible to envisage units that operate with a larger number of zones, in connection with the multiplication of injection or draw-off points.

For the adsorption column that is part of the device according to the invention, the concept of zone is defined by time period in the following manner:

Zone 4: Time period encompassed between the end of the injection of the desorbent and the beginning of the draw-off of the raffinate Zone 3: Time period encompassed between the beginning of the draw-off of the raffinate and the end of the injection of the feedstock Zone 2: Time period encompassed between the end of the injection of the feedstock and the beginning of the draw-off of the extract Zone 1: Time period encompassed between the beginning of the draw-off of the extract and the end of the injection of the desorbent.

For the device according to the invention, a cycle is defined as being the time period passing between two successive injections of desorbent.

It is also possible to break down the cycle of the device according to the invention into elementary stages.

At any time in a cycle of the device according to the invention, one of the tanks that are part of the device is used to supply the column and another tank that is separate from the first is used to store the effluent that is obtained from the column.

An elementary stage is defined by the simultaneous change of the tank that is used for the supply of the column (called supply tank) and the tank that is used for the storage of the effluent of the column (called storage tank).

The device according to the invention comprises:

An adsorbent column (C4) and a catalyst column (R6) in the case of the first variant, or a single column CR4 that contains a mixture of catalyst and adsorbent in the case of the second variant;

A number of storage tanks (B23) to (B34). The minimum tank number is equal to the number of zones that the reactive separation unit in a reactive simulated moving bed that it is desired to study has, generally four zones. Preferably, the number of tanks is greater than the number of beds that are present in the unit in the reactive simulated moving bed that it is desired to study.

A pump that is placed on the line (3) or (47);

A number of injection lines (1), (2), connected to at least one pump and a valve on each line (not shown in FIGS. 1 and 2);

A number of draw-off lines (9), (10) that are connected to at least one flow regulation system (for example, a mass flow rate regulator not shown in FIGS. 1 and 2), and a valve on each line.

At each moment of the cycle of the device according to the invention, one of the tanks, said supply tank, is used to supply the column, and another tank that is separate from the supply tank, said storage tank, is used to store the effluent that is obtained from said column (CR4).

During the supply, the contents of the supply tank are gradually replaced by a cover gas (for example nitrogen, argon or helium). When, at another moment of the cycle, this tank will be used as a storage tank, the cover gas will be gradually eliminated.

This system can operate at a temperature between the ambient temperature and 350° C.

For this purpose, it is possible to heat the entire system in a single heating device (for example by immersing the device in an oil bath).

In the case of the first variant, it is possible to dissociate the temperature of the catalytic reactor from the remainder of the device by employing a second heating device that is dedicated to the reactor. It is also possible to monitor the temperature of each tank and each column independently.

The experimental device can comprise a system for rinsing the common line for draw-off of the contents of tanks (47). The pollution of flows obtained from tanks by the fluid stagnating in this line is thus avoided.

The system can also comprise equipment making possible the rinsing of injection lines (11) to (22) and draw-off lines (35) to (46) of the contents of the tanks.

The device conceived according to the first variant of the invention advantageously comprises a system for rinsing the short-circuit line (7) and the column filled with catalyst (R6).

A liquid that is not adsorbed in the adsorbent that is used and that does not react in the catalyst or in any other body or radical that is present in the system is preferably used for the different stages of rinsing that are presented in detail above.

It is also possible to use any mixture that consists of radicals that are present in the system, such as, for example, the desorbent, the feedstock or a mixture of these two effluents.

The dead volume that is obtained by rinsing can be either eliminated or reinjected at a point of the system.

The valves that are used are advantageously all-or-nothing valves.

So as to follow the behavior of the system, the latter advantageously comprises a line analysis device, for example by gas phase chromatography, preferably placed on line (8).

It is also possible to carry out these analyses on lines (3), (5) or (47).

Lines advantageously can be placed on the tanks so as to be able to draw off a small amount for analysis.

Principle of Operation of the Invention According to the First Variant

The principle of the invention will be better understood upon examination of FIG. 1, which shows a diagrammatic embodiment of the experimental device according to the first variant of the invention with an adsorption column (C4) and a catalytic column (R6) that is separate from the adsorption column.

At any moment of a cycle of the device according to the invention, a tank of the series of 12 tanks shown in FIG. 1 is used to supply the column C4, and another tank that is separate from the preceding one is used for storing the effluent that is obtained from column C4 or R6.

An elementary stage is defined by the simultaneous change of the tank that is used for the supply of the column and the tank used for the storage of the effluent of the column.

During the first cycle, the filling order of the tanks is selected, whereby this order is then maintained for the following cycles.

The selection of the storage tanks along a cycle results from that of the supply tanks according to the following rule:

In the case where the catalytic column R6 is in operation, at any stage n of a cycle, the adsorbent column (C4) is supplied by means of the line (3) by the contents of the tank that was filled by means of the line (8) by the output effluent of the catalytic column (R6) that corresponds to the stage (n+1) of the preceding cycle.

During the last stage of the cycle, the adsorbent column (C4) is supplied by means of the line (3) by the contents of the tank that was filled by means of the line (8) via the output effluent of the catalytic column (R6) that corresponds to the first stage of the preceding cycle.

In the case where the catalytic column R6 is short-circuited, at any stage n of a cycle, the adsorbent column (C4) is supplied by means of the line (3) by the contents of the tank that was filled by means of the line (8) by the output effluent of the column (C4) that corresponds to the stage (n+1) of the preceding cycle. During the last stage of the cycle, the adsorbent column (C4) is supplied by means of the line (3) by the contents of the tank that was filled by means of the line (8) by the output effluent of the column (C4) that corresponds to the first stage of the preceding cycle.

In the particular case of a balanced reaction that leads to a single product, the catalytic column R6 is used only during a portion of the cycle. Depending on whether the only product is most heavily retained by the adsorbent or least heavily retained by the adsorbent, this product is separated in the extract or the raffinate respectively. Thus, When the column (C4) operates in zone 1, 2 or 4 (the case where the product of the reaction is the most heavily retained by the adsorbent) or in zone 1, 3 or 4 (case where the product of the reaction is the least heavily retained by the adsorbent), the output flux of the column (C4) is directly introduced into a storage tank by short-circuiting the catalyst column (R6) by means of the line (7).

At the beginning of the period during which the column (C4) operates in zone 3, a portion of the output flow of the adsorbent column (C4) is drawn off via the line (10). This flow corresponds to the raffinate.

During the remainder of the period during which the column (C4) operates in zone 3, the output effluent of the column (C4) is introduced into the catalyst column (R6).

In all of the other cases, and in particular when the operating conditions of the adsorption column (C4) and the reactive column (R6) are different, the catalytic column (R6) is never short-circuited.

The concept of zone for the device according to the invention is defined by time periods in the following manner:

Zone 4: Time period encompassed between the end of injection of the desorbent and the beginning of the draw-off of the raffinate Zone 3: Time period encompassed between the beginning of the draw-off of the raffinate and the end of injection of the feedstock Zone 2: Time period encompassed between the end of injection of the feedstock and the beginning of draw-off of the extract;

Zone 1: Time period encompassed between the beginning of the draw-off of the extract and the end of injection of the desorbent.

At the beginning of the period during which the adsorbent column (C4) operates in zone 1, a portion of the output flow of the columns is drawn off via the line (9). This flow corresponds to the extract.

At the end of the period during which the adsorbent column (C4) operates in zone 1, a desorbent flow is introduced at the inlet of the column (C4) via the line (2), in addition to the flow obtained from one of the storage tanks.

At the beginning of the period during which the adsorbent column (C4) operates in zone 3, a portion of the output flow of the columns is drawn off via the line (10). This flow corresponds to the raffinate.

At the end of the period during which the adsorbent column (C4) operates in zone 3, a feedstock flow is introduced at the inlet of the column (C4) via the line (1), in addition to the flow obtained from one of the storage tanks.

The description of an operating mode of the device according to the invention below is provided by way of the illustration of the invention but in no way limits the scope of said invention.

Unit to be Studied

The unit to be studied is typically a unit of the reactive simulated moving bed type diagrammed in FIG. 3, comprising 12 adsorbent beds (C1 to C12) and 2 catalyst beds (R1 and R2).

This unit is adapted specifically to the case of a reaction leading to a single product (for example, A ↔ B), where it is desired to recover in the extract E the most heavily retained pure product. The 12 stages of the cycle were shown in the order of 1 to 12. Each stage of the cycle corresponds to a position of the injection and draw-off points along the different beds. Each stage of the cycle corresponds correlatively to the movement of the catalytic beds R1 and R2.

We selected a total of 12 adsorbent beds distributed at a rate of three beds per zone. The unit makes it possible to change the positions of the catalytic beds (R1 and R2) so that the latter are always located within zone 3 between the first and second adsorbent beds for the catalytic bed R1 and between the second and third adsorbent beds for the catalytic bed R2.

Device According to the Invention

The application of the device according to the invention to the study of the unit described in the preceding paragraph is illustrated by FIG. 1.

The device consists of a column that is filled with adsorbent (C4), a column that is filled with catalyst (R6), and twelve storage tanks (B23 to B34). The device operates according to the cycle that is described in Table 1.

Each column of Table 1 corresponds to a stage of the cycle in the direction of the device.

In the case that is presented, each zone corresponds to 3 stages.

Each stage corresponds essentially to the selection of a supply tank and a draw-off tank.

For example, in stage 1, the tank 31 is used as a storage tank, and the tank 30 is used as a supply tank.

Table 1 shows a "diagonal" change of the supply and draw-off tanks that corresponds to the rule:

At any stage n of a cycle, the adsorbent column (C4) is supplied by the contents of the tank that has been filled by the output effluent of the catalytic column (R6) that corresponds to the stage (n+1) of the preceding cycle. During the last stage of the cycle, the adsorbent column (C4) is supplied by the contents of the tank that has been filled by the output effluent of the catalytic column (R6) that corresponds to the first stage of the preceding cycle.

TABLE 1

Description of the cycle followed by the device according to the invention
and according to the first variant of operation

| | Zone 3 | | | Zone 2 | | | Zone 1 | | | Zone 4 | | |
|---|---|---|---|---|---|---|---|---|---|---|---|---|
| | Stage 1 | Stage 2 | Stage 3 | Stage 4 | Stage 5 | Stage 6 | Stage 7 | Stage 8 | Stage 9 | Stage 10 | Stage 11 | Stage 12 |
| Feedstock 1 | X | X | O | X | X | X | X | X | X | X | X | X |
| Desorbent 2 | X | X | X | X | X | X | X | X | O | X | X | X |
| Extract 9 | X | X | X | X | X | X | O | X | X | X | X | X |
| Raffinate 10 | O | X | X | X | X | X | X | X | X | X | X | X |
| Column C4 | O | O | O | O | O | O | O | O | O | O | O | O |
| Column R6 | X | O | O | X | X | X | X | X | X | X | X | X |
| Tank B34 | X | X | X | X | X | X | X | X | A | S | X | X |
| Tank B33 | X | X | X | X | X | X | X | X | X | A | S | X |
| Tank B32 | X | X | X | X | X | X | X | X | X | X | A | S |
| Tank B31 | S | X | X | X | X | X | X | X | X | X | X | A |
| Tank B30 | A | S | X | X | X | X | X | X | X | X | X | X |
| Tank B29 | X | A | S | X | X | X | X | X | X | X | X | X |
| Tank B28 | X | X | A | S | X | X | X | X | X | X | X | X |
| Tank B27 | X | X | X | A | S | X | X | X | X | X | X | X |
| Tank B26 | X | X | X | X | A | S | X | X | X | X | X | X |
| Tank B25 | X | X | X | X | X | A | S | X | X | X | X | X |
| Tank B24 | X | X | X | X | X | X | A | S | X | X | X | X |
| Tank B23 | X | X | X | X | X | X | X | A | S | X | X | X |

A: Supply tank, S: Storage tank, O: Used, X: Isolated.

Principle of Operation of the Device According to the Second Variant

The principle of the invention will be better understood upon examination of FIG. 2, which shows a schematic embodiment of the experimental device according to the second variant of the invention with a single catalytic adsorption column (CR4).

Let us recall that at any time in a cycle of the device according to the invention, a tank of the series of the 12 tanks shown in FIG. 1 is used to supply the column CR4, and another tank separate from the preceding one is used to store the effluent that is obtained from the column CR4.

An elementary stage is defined by the simultaneous change of the tank that is used for the supply of the column and the tank that is used for the storage of the effluent of the column CR4.

During the first cycle, the order of filling of the tanks is selected, whereby this order is then maintained for the following cycles.

The selection of the storage tanks along a cycle results from that of the supply tanks according to the following rule:

At any stage n of a cycle, the column (CR4) is supplied by means of the line (3) by the contents of the tank that has been filled by means of the line (8) by the output effluent of the column (CR4) that corresponds to the stage (n+1) of the preceding cycle. During the last stage of the cycle, the column (CR4) is supplied by means of the line (3) by the contents of the tank that has been filled by means of the line (8) by the output effluent of the column (CR4) that corresponds to the first stage of the preceding cycle.

Let us recall that the concept of zone for the device according to the invention is defined by time periods in the following manner:

Zone 4: Time period encompassed between the end of injection of the desorbent and the beginning of the draw-off of the raffinate Zone 3: Time period encompassed between the beginning of the draw-off of the raffinate and the end of injection of the feedstock Zone 2: Time period encompassed between the end of injection of the feedstock and the beginning of the draw-off of the extract Zone 1: Time period encompassed between the beginning of the draw-off of the extract and the end of injection of the desorbent.

At the beginning of the period during which the column (CR4) operates in zone 1, a portion of the output flow from the column is drawn off via the line (9). This flow corresponds to the extract.

At the end of the period during which the column (CR4) operates in zone 1, a desorbent flow is introduced at the input of column (CR4) via the line (2), in addition to the flow that is obtained from one of the storage tanks.

At the beginning of the period during which the column (CR4) operates in zone 3, a portion of the output flow of the column is drawn off via the line (10). This flow corresponds to the raffinate.

At the end of the period during which the column (CR4) operates in zone 3, a feedstock flow is introduced at the input of the column (CR4) via the line (1), in addition to the flow that is obtained from one of the storage tanks. The description of a mode of operation of the device according to the invention below is provided by way of illustration of the invention but in no way limits the scope of said invention.

Unit to be Studied

The unit to be studied is a unit of the reactive simulated moving bed type that is shown in a diagram in FIG. 4, comprising 12 beds filled with a mixture of adsorbent and catalyst (CR1 to CR12).

This unit is specifically adapted to the case of a reaction that leads to two or more products (for example, A (+B) ⇌ C+D) where it is desired to recover in the extract E the most heavily retained pure product. The 12 stages of the cycle were shown in the order of 1 to 12. Each stage corresponds to a position of points of injection and draw-off along different beds.

We selected a total of 12 adsorbent beds distributed at a rate of three beds per zone.

Device According to the Invention

The application of the device according to the invention in the study of the unit described in the preceding paragraph is illustrated by FIG. 2.

The device consists of a column that is filled with adsorbent and catalyst (CR4) and twelve storage tanks (B23 to B34). The device operates according to the cycle that is described in Table 2.

Each column of Table 2 corresponds to a stage of the cycle in terms of the device.

In the case that is presented, each zone corresponds to 3 stages.

Each stage corresponds essentially to the selection of a supply tank and a draw-off tank. For example, in stage 1, the tank 31 is used as a storage tank, and the tank 30 is used as a supply tank. Table 2 shows a "diagonal" change of the supply and draw-off tanks that corresponds to the rule:

At any stage n of a cycle, the column (CR4) is supplied by the contents of the tank that has been filled by the output effluent of the column (CR4) that corresponds to the stage (n+1) of the preceding cycle. During the last stage of the cycle, the column (CR4) is supplied by the contents of the tank that has been filled by the output effluent of the column (CR4) that corresponds to the first stage of the preceding cycle.

Table 3 illustrates a device according to the invention that contains only 6 tanks.

Whereby the stages and the zones are defined by different events (the beginnings and ends of injection for the zones and the changes of tanks for the stages), the zones are not always comprised of a whole number of stages.

TABLE 3

Description of the cycle followed by the device according to the invention and according to the second variant of operation-Case of a cycle where the number of tanks is less than the number of beds of the reactive simulated moving bed unit that is studied.

|  | Zone 3 | | Zone 2 | Zone 1 | | Zone 4 |
| --- | --- | --- | --- | --- | --- | --- |
|  | Stage 1 | Stage 2 | Stage 3 | Stage 4 | Stage 5 | Stage 6 |
| Feedstock 1 | X | X | O | X | X | X |
| Desorbent 2 | X | X | X | X | O | X |
| Extract 9 | X | X | X | O | X | X |
| Raffinate 10 | O | X | X | X | X | X |
| Column CR4 | O | O | O | O | O | O |
| Tank B28 | A | S | X | X | X | X |
| Tank B27 | X | A | S | X | X | X |
| Tank B26 | X | X | A | S | X | X |
| Tank B25 | X | X | X | A | S | X |
| Tank B24 | X | X | X | X | A | S |
| Tank B23 | S | X | X | X | X | A |

A: Supply tank, S: Storage tank, O: Used, X: Isolated

Exploitation of the Results of the Device According to the Invention

To exploit the results obtained from the experimental device according to the invention for the purpose of the study

TABLE 2

Description of the cycle followed by the device according to the invention and according to the second variant of operation-Case of a cycle where the number of tanks is equal to the number of beds of the reactive simulated moving bed unit that is studied.

|  | Zone 3 | | | Zone 2 | | | Zone 1 | | | Zone 4 | | |
| --- | --- | --- | --- | --- | --- | --- | --- | --- | --- | --- | --- | --- |
|  | Stage 1 | Stage 2 | Stage 3 | Stage 4 | Stage 5 | Stage 6 | Stage 7 | Stage 8 | Stage 9 | Stage 10 | Stage 11 | Stage 12 |
| Feedstock 1 | X | X | O | X | X | X | X | X | X | X | X | X |
| Desorbent 2 | X | X | X | X | X | X | X | X | O | X | X | X |
| Extract 9 | X | X | X | X | X | X | O | X | X | X | X | X |
| Raffinate 10 | O | X | X | X | X | X | X | X | X | X | X | X |
| Column CR4 | O | O | O | O | O | O | O | O | O | O | O | O |
| Tank B34 | X | X | X | X | X | X | X | X | A | S | X | X |
| Tank B33 | X | X | X | X | X | X | X | X | X | A | S | X |
| Tank B32 | X | X | X | X | X | X | X | X | X | X | A | S |
| Tank B31 | S | X | X | X | X | X | X | X | X | X | X | A |
| Tank B30 | A | S | X | X | X | X | X | X | X | X | X | X |
| Tank B29 | X | A | S | X | X | X | X | X | X | X | X | X |
| Tank B28 | X | X | A | S | X | X | X | X | X | X | X | X |
| Tank B27 | X | X | X | A | S | X | X | X | X | X | X | X |
| Tank B26 | X | X | X | X | A | S | X | X | X | X | X | X |
| Tank B25 | X | X | X | X | X | A | S | X | X | X | X | X |
| Tank B24 | X | X | X | X | X | X | A | S | X | X | X | X |
| Tank B23 | X | X | X | X | X | X | X | A | S | X | X | X |

A: Supply tank, S: Storage tank, O: Used, X: Isolated.

of a reactive simulated moving bed unit, it is necessary to extrapolate the performance levels of the device according to the invention based on the number of storage tanks.

Actually, it is known that the behavior of a simulated moving bed unit is identical to that of a device that consists of an adsorbent column and a high number of storage tanks.

It has also been shown that the extrapolation of the number of storage tanks remains valid in the case where the experimental device comprises a reaction zone that may or may not be separated from the adsorption zone, as is the case of the device according to the invention.

In the description below, N refers to the number of tanks of the device according to the invention and m refers to the number of adsorbent beds (or the adsorbent/catalyst mixture) of the reactive simulated moving bed unit that is being studied.

The extrapolated number of tanks of the device according to the invention is called nk, i.e., the number of tanks that is optionally varied in the formulas that make it possible to predict the performance level of the studied LMS unit P (LMSR) from the performance observed in the device according to the invention P(N). nk is therefore different from the actual number of tanks N, and will in general be greater than it is during extrapolation. Performance P is called the yield or the purity of the desired product or products, whereby P(N) is the performance level experimentally observed in the device that is the object of this invention, and P(LMSR) is the performance level that is projected on the simulated moving bed unit that is studied.

The performance level of the device P(N) is known by experiment.

The performance of the LMS unit to be studied is simulated from the performance P(N) by extrapolating with a number of tanks $n_k$ of more than N.

The number of tanks nk in the extrapolation of the device according to the invention is preferably selected as a multiple of the number m, or nk=m*k.

The relative deviation Δ between the performance levels obtained with the numbers of tanks (m)k and (m+1)k and, when the latter is less than or equal to ε%, the calculated performance levels, are considered to be equal to that of the unit in a reactive simulated moving bed.

If the purity performance, which is denoted as P(nk), is selected for the device according to the invention with extrapolation with nk tanks, for example, and $P^{LSMR}$ is selected for the reactive simulated moving bed unit as soon as the value of nk is such that:

$$\Delta = \frac{P(n_{k+1}) - P(n_k)}{P(n_k)} \leq \varepsilon$$

then $$P(n_{k+1}) \cong P(n_k) \cong P^{LMSR}$$

In general, ε=0.01% is selected, and preferably ε=0.001% is selected.

It is also possible to use the experimental results of the device according to the invention to establish a relationship that makes it possible to calculate the relative deviation of performance levels between the device according to the invention and the reactive simulated moving bed unit, denoted as $\Delta_{nk/LMSR}$ based on the number of tanks $n_k$ selected.

If the purity performance level that is denoted as P is selected, for example, this relationship is written:

$$\Delta_{nk/LMSR} = \frac{P(n_k) - P^{LMSR}}{P^{LMSR}} = -a.\exp(-b.n_k) = a.\exp(-b.m.k)$$

in which a and b are two positive real numbers that are calculated from experimental results of the device according to the invention comprising N tanks.

The relationship that connects the performance levels of the device according to the invention to those of the reactive simulated moving bed unit is thus established via the number of tanks $n_k$=m, k of the device.

If the purity performance level that is denoted as P is selected, for example, this relationship is written:

$$P(n_k) = P^{LMSR}(1 - a.\exp(-b.m.k))|$$

Starting from this relationship, the performance levels of the reactive simulated moving bed unit that is studied is estimated by giving sufficiently high values to k. In practice, when k is higher than 10, and preferably higher than 20, the performance levels that are calculated for the device according to the invention are equal to those of the reactive simulated moving bed unit that is studied, i.e., the relative deviation between the calculated performance levels and the performances of the unit to be studied is less than 0.01% and preferably less than 0.001%.

EXAMPLE 1

So as to illustrate the methodology described above, the device is used according to the invention to study a xylene separation/isomerization unit.

The reactive simulated moving bed (that will be called an LMSR unit), which it is desired to show by means of the device according to the invention, is composed of 24 beds filled with adsorbent (faujasite X-type zeolite with barium exchange) distributed into 4 zones: 6 beds in the first zone, 9 beds in the second zone, 6 beds in the third zone, and 3 beds in the fourth zone.

The LMSR unit that was studied comprises in addition 5 beds filled with catalyst ZSM-5 (MFI-type zeolite) that are interposed between the adsorbent beds of the zone 3.

The adsorbent and catalyst beds have the same geometry: length 1.13 m and internal section 3.5 cm².

The feedstock, composed of 23.9% of para-xylene, and 76.1% of a mixture of ortho-xylene and meta-xylene, is introduced at a flow rate of 15.455 cm³/minute.

The desorbent (para-diethyl benzene) is introduced with a flow rate of 102.73 cm³/minute. A flow rate of extract of 49.23 cm³/minute and a flow rate of raffinate of 68.95 cm³/minute are sampled.

The flow rate of zone 1 is 287.03 cm³/minute. The period or duration of a stage is 70.8 seconds.

The temperature is maintained at 493 K, and the pressure is monitored so that it is in liquid phase at any point of the device.

This unit produces an extract that contains pure para-xylene at 99.81% with a yield (calculated relative to the amount of introduced para-xylene) of 198.2%.

The device according to the invention corresponds to the variant 1 shown by FIG. 1.

It consists of two columns in a series of length 1.13 m and of internal section 3.5 cm², whereby the first (C4) is filled with adsorbent (faujasite X-type zeolite with barium exchange), whereby the second (R6) is filled with ZSM-5 catalyst (MFI-type catalyst).

The device comprises 24 tanks of 1.5-liter volume, or as many beds as the unit to be studied comprises.

The tanks and the columns are kept at 493 K, and the pressure is monitored such that it is in liquid phase at any point of the device.

The device according to the invention therefore comprises only 2 columns rather than 29 in the unit to be studied.

The feedstock, composed of 23.9% of para-xylene and 76.1% of a mixture of ortho-xylene and meta-xylene, is introduced at a flow rate of 15.455 cm³/minute. The desorbent (para-diethyl benzene) is introduced with a flow rate of 102.73 cm³/minute.

A flow rate of extract of 49.23 cm³/minute is sampled, and a flow rate of raffinate of 68.95 cm³/minute is sampled. The flow rate of zone 1 is 287.03 cm³/minute, and the period is 70.8 seconds.

The flows are not injected continuously, but a single time per cycle, and the contents of the tanks are reintroduced into the first column.

The device according to the invention leads to the following performances without extrapolation:

A purity of the para-xylene in the extract of 90.13% and an overall para-xylene yield of 181.68%.

After extrapolation by simulation with 240 tanks, a purity of 99.80% and a yield of 198.2% are obtained, whereas the reactive simulated moving bed unit that comprises 24 adsorbent beds and 5 catalyst beds located in zone 3 leads to the following performance levels: a purity of 99.81% and a para-xylene yield of 198.2%.

The relationship between the performance levels of the device according to the invention, those of the reactive simulated moving bed unit, and the number of tanks $n_k$=24.k of the device is written for the purity:

$$P(n_k) = P^{LMSR}(1 - 0{,}233.\exp(-0{,}0356.24.k))$$

The device according to the invention, with 24 tanks in this example, therefore makes it possible, with a number of columns limited to one or two, to reproduce the results of the unit to be studied comprising 24 beds, by extrapolating the results that are obtained with said device by means of the number of tanks and to come as close as desired to the results of the unit to be studied.

EXAMPLE 2

This example illustrates a variant of the method of exploitation of the results of the device according to the invention in which the number of tanks of the device is less than the number of beds of the reactive simulated moving bed unit that it is desired to study.

The reactive simulated moving bed unit has the same characteristics as in Example 1, or 24 beds distributed into 4 zones. This unit produces an extract containing pure para-xylene at 99.81% with a yield (calculated relative to the amount of para-xylene that is introduced) of 198.2%.

The device according to the invention corresponds to the variant 1 that is shown by FIG. 1.

It consists of two columns in a series of length 1.13 m and of internal section 3.5 cm², whereby the first (C4) is filled with adsorbent (faujasite X-type zeolite with barium exchange), and the second (R6) is filled with catalyst ZSM-5 (MFI-type zeolite).

The device comprises only 8 tanks of 1.5-liter volume. The tanks and the columns are maintained at 493 K, and the pressure is monitored so as to operate in liquid phase at any point of the device.

The device according to the invention therefore comprises only 2 columns rather than 29 in the unit to be studied.

The feedstock, consisting of 23.9% of para-xylene, and 76.1% of a mixture of ortho-xylene and meta-xylene, is introduced with a flow rate of 15.455 cm³/minute. The desorbent (para-diethyl benzene) is introduced with a flow rate of 102.73 cm³/minute.

A flow rate of extract of 49.23 cm³/minute is sampled, and a flow rate of raffinate of 68.95 cm³/minute is sampled. The flow rate of zone 1 is 287.03 cm³/minute, and the period is 70.8 seconds.

The flows are not injected continuously but a single time per cycle, and the content of the tanks is reintroduced into the first column.

The device according to the invention leads without extrapolation into the following performance levels:

A purity of para-xylene in the extract of 83.07% with an overall yield of para-xylene of 167.5%.

After extrapolation by simulation with 240 tanks, a purity of 99.80% and a yield of 198.2%, are obtained, whereas a reactive simulated moving bed unit that comprises 24 beds of adsorbent and 5 beds of catalyst located in zone 3 leads to the following performance levels; a purity of 99.81% and a yield of para-xylene of 198.2%.

The relationship between the performance levels of the device according to the invention, those of the reactive simulated moving bed unit and the number of tanks $n_k$=8.k of the device is written for the purity:

$$P(n_k) = P^{LMSR}(1 - 0{,}223.\exp(-0{,}0356.8*k))$$

The device according to the invention, with 8 tanks in this example, therefore makes it possible, with a number of columns limited to one or two, to reproduce the results of the unit to be studied with 24 beds, by extrapolating the results that are obtained with said device by means of the number of tanks and to come as close as desired to the results of the unit to be studied.

The invention claimed is:

1. A process for the study and the extrapolation of an industrial or pilot unit that operates in a reactive simulated moving bed wherein a feedstock and a desorbent are supplied and an extract and a raffinate are withdrawn according to periods of time called zones and defined in the following manner:

Zone 1: Time period encompassed between beginning of draw-off of the extract and end of injection of the desorbent, Zone 2: Time period encompassed between end of injection of the feedstock and beginning of the draw-off of the extract, Zone 3: Time period encompassed between beginning of draw-off of the raffinate and end of injection of the feedstock, Zone 4: Time period encompassed between the end of the injection of the desorbent and the beginning of the draw-off of the raffinate, said process comprising providing a device that comprises a first column (C4) that contains the adsorbent, a second column (R6) that contains catalyst and a number of tanks (B23 to B34) for supplying of the adsorption column (C4) and for storage of the effluent obtained from catalytic column (R6), except for certain stages of the cycle where said catalytic column is short-circuited, a cycle of said process being defined as the period of time between two successive desorbent injections and being divided into elementary stages, each elementary stage being defined by the simultaneous exchange of the tank that is used for the supply of the column and the tank that is used for the storage of the effluent of the column (R6), and the device being characterized by the number of tanks that is at least equal to the number of zones of the simulated moving bed unit being studied, whereby the process operates according to a cycle that is defined as with each stage n of said cycle, with the exception of the latter, the adsorbent column (C4) is supplied by the contents of the tank that has been filled by the flow of output from the column (R6) (or by the flow of output from the column (C4) when the column (R6) is short-circuited), corresponding to the stage (n+1) of the preceding cycle, and by the fact that in the last stage of the cycle, the adsorbent column (C4) is supplied by the content of the tank that has been filled by the flow of output from the column (R6), or by the flow of output from the column (C4) if the column (R6) is short-circuited, corresponding to the first stage of the preceding cycle.

2. A process comprising an experimental device for the study and the extrapolation of an industrial or pilot unit operating in a reactive simulated moving bed according to claim 1, in which the column that contains the adsorbent and the column that contains the catalyst are combined into a single column (CR4) that contains a mixture of adsorbent and catalyst, whereby said device contains a number of tanks (B23 to B34) that are used in the supply of the column (CR4) and in the storage of the effluent that is obtained from said column, and whereby the cycle of the device is defined by the fact that with each stage n of said cycle, with the exception of the latter, the adsorbent column (CR4) is supplied by the contents of the tank that has been filled by the flow of output from the column (CR4) corresponding to the stage (n+1) of the preceding cycle, and by the fact that in the last stage of the cycle, the adsorbent column (CR4) is supplied by the contents of the tank that has been filled by the flow of output from the column (CR4) that corresponds to the first stage of the preceding cycle.

3. A process according to claim 1, in which the number of tanks is at least equal to the number of zones of a unit that operates as a reactive simulated moving bed.

4. A process according to claim 1 in which the number of tanks is a whole number of the number of adsorbent beds of a unit operating as a reactive simulated moving bed.

5. A process according to claim 1 comprising separating xylene isomers.

6. A process according to claim 1 comprising separating linear paraffins form a mixture with branched and aromatic hydrocarbons.

7. A process according to claim 1 comprising separating olefins form a mixture with paraffins.

8. A process according to claim 3 wherein the number of tanks is at least equal to the number of adsorbent beds of a unit operating as a reactive simulated moving bed.

9. A process according to claim 1, further comprising collecting purity data from said process and extrapolating such data to design a larger SMB unit.

* * * * *